US005637616A

United States Patent [19]

Sharpe et al.

[11] Patent Number: 5,637,616
[45] Date of Patent: Jun. 10, 1997

[54] METHOD FOR TREATING DISEASES MEDIATED BY PROTEASES

[75] Inventors: Richard J. Sharpe, Gloucester; Maureen H. McAloon, Boston; Stephen J. Galli, Winchester; Kenneth A. Arndt, Newton Centre, all of Mass.

[73] Assignee: Arcturus Pharmaceutical Corporation, Woburn, Mass.

[21] Appl. No.: 131,892

[22] Filed: Oct. 5, 1993

Related U.S. Application Data

[63] Continuation-in-part of Ser. No. 79,645, Jun. 18, 1993, abandoned.

[51] Int. Cl.$^6$ .................... C07C 323/59; A61K 31/195; A61K 31/20
[52] U.S. Cl. .................... 514/562; 514/28; 514/29; 514/30; 514/251; 514/291; 514/457; 514/513; 514/538; 514/549; 514/552; 514/554; 514/555; 554/85; 554/101; 554/102; 558/230; 558/256; 558/257; 560/16; 560/147; 560/153; 562/426; 562/557
[58] Field of Search .................... 562/556, 426, 562/557; 514/562, 28, 29, 30, 251, 291, 457, 513, 538, 549, 552, 554, 555; 554/85, 101, 102; 558/230, 256, 257; 560/16, 147, 153

[56] References Cited

U.S. PATENT DOCUMENTS

| | | | |
|---|---|---|---|
| 4,354,023 | 10/1982 | Falciani et al. | 544/30 |
| 4,414,387 | 11/1983 | Broggi et al. | 544/28 |
| 4,440,788 | 4/1984 | Terayama et al. | 424/320 |
| 4,476,120 | 10/1984 | Gonella | 424/180 |
| 4,567,163 | 1/1986 | Ponchiroli | 514/29 |
| 4,847,282 | 7/1989 | Deboeck | 514/400 |
| 4,861,764 | 8/1989 | Samour et al. | 514/177 |
| 4,970,236 | 11/1990 | Ziggiotti et al. | 514/562 |
| 5,073,641 | 12/1991 | Bundgaard et al. | 560/56 |
| 5,080,906 | 1/1992 | Carenzi et al. | 424/452 |
| 5,124,062 | 6/1992 | Stevens | 252/162 |
| 5,173,510 | 12/1992 | Bloom et al. | 514/616 |
| 5,182,271 | 1/1993 | Houlihan | 514/77 |
| 5,212,316 | 5/1993 | Spinelli et al. | 546/278 |
| 5,256,408 | 10/1993 | Babcock et al. | 424/78.04 |
| 5,296,500 | 3/1994 | Hillebrand | 514/562 |

FOREIGN PATENT DOCUMENTS 0 554 708 A1  8/1993  European Pat. Off. .

OTHER PUBLICATIONS

Abdel-Rahman R.M. et al., "Synthesis of Some New Thioesters of 1,2,4-Triazine-3-Hydrazones and Assays for their Anticancer and Anti Human Immune Virus Activities," *Il Farmaco*, 1993, vol. 48 (3), pp. 397–406.

Ahmed, A.R., et al., mod., UCLA Conference, "Pemphigus: Current Concepts," *Annals of Internal Medicine*, 1980, vol. 92, pp. 396–405.

Anhalt, Labib, Voorhees, Beals and Diaz, "Induction of Pemphigus in Neonatal Mice by Passive Transfer of I$_G$G From Patients with the Disease," *N. Engl. J. Med.* 1982, vol. 306, pp. 1189–1196.

Anhalt, Till, Diaz, Labib, Patel and Eaglstein, "Defining the Role of Complement in Experimental *Pemphigus vulgaris* in Mice," *J. Immunol.* 1986, vol. 137, pp. 2835–2840.

Arndt, K. "Lichen planus," Fitzpatrick, Eisen, Wolff, Freedberg and Austen, *Dermatology in General Medicine*, 1987, vol. 1, McGraw–Hill, Inc., New York, pp. 967–973.

Arndt, K.A., Mendenhall, P.V., "The Pharmacology of Topical Therapy", *Dermatology in General Medicine*, 1987; Fitzpatrick, Eisen, Wolff, Freeberg, Austen, eds., 3d ed., McGraw Hill, Inc., New York, pp. 582–584, 2532–2540.

Aruoma, O.I., et al., "The Antioxidant Action of N–Acetylcysteine: Its Reaction with Hydrogen Peroxide, Hydroxyl Radical, Superoxide, and Hypochlorous Acid," *Free Radical Biology & Medicine*, vol. 6, 1989, pp. 593–597.

Baden, L.A., "Bullous pemphigoid," *Manual of Clinical Problems in Dermatology*, Little, Brown & Co., Boston, 1992, p. 54.

Banks, B.J., et al., "Phenylthionitromethane; a Versatile Reagent for the Conversion of Aldehydes into α–Substituted S–Phenyl Thioesters," *J. Chem. Soc., Chem. Commun.*, 1984, p. 670.

Barnhart, et al., "Proteases in Inflammation," *Annals of N.Y. Acad. Sci.*, 1968, pp. 526–539.

Berggren, M., et al., "Glutathione biosynthesis in the isolated perfused rat lung: utilization of extracellular glutathione," *FEBS Lett.*, 1984, vol. 176, pp. 189–192.

Betageri, G.V., et al., "Drug Delivery Using Antibody–Liposome Conjugates," *Drug Development and Industrial Pharmacy* 1993, vol. 19, No. 16, 2109–2116.

Bigby, S.M., and Arndt, K.A, "Chronic Oral Ulcerations," *Manual of Clinical Dermatology*, Little, Brown & Co., Boston, 1992, pp. 314–315.

Bleicher, P.A., "Lichen planus and Related Disorders," *Manual of Clinical Problems in Dermatology*, Olbricht, Bigby and Arndt, eds. 1992, Little, Brown & Co., Boston, pp. 85–89.

Christophers, E., et al., "Psoriasis," *Dermatology in General Medicine*, 1987; Fitzpatrick, Eisen, Wolff, Freeberg, Austen, eds., 3d ed., McGraw Hill, Inc., New York, pp. 461–491.

(List continued on next page.)

*Primary Examiner*—Peter O'Sullivan
*Attorney, Agent, or Firm*—Kilpatrick & Cody, L.L.P.

[57] ABSTRACT

A method for the topical or systemic treatment of disorders mediated by proteases which result in skin or mucosal lesions, and in particular, pemphigus, cicatricial pemphigoid, bullous pemphigoid, lichen planus, and canker sores, is disclosed wherein the host is treated with an effective amount of N-acetyl ysteine or a derivative thereof, or its pharmaceutically acceptable salt, optionally in a pharmaceutically acceptable diluent or carrier for systemic or topical delivery.

48 Claims, No Drawings

OTHER PUBLICATIONS

Dubertret, L., et al., "Localization of Proteolytic Activity in Psoriatic Skin," *British Journal of Dermatology* 1992, vol. 107, pp. 499–504.

Eisen, Ellis, Duell, Griffiths and Voorhees, "Effect of Topical Cyclosporine Rinse on Oral *Lichen planus,*" *N. Engl. J. Med.,* 1990, vol. 323, pp. 290–294.

Ellis, Dodson, Police, "Restoration of Cerebrovascular Responsiveness to Hyperventilation by the Oxygen Radical Scavenger N–Acetycsteine Following Experimental Traumatic Brain Injury," *J. Neurosurg.,* 1991, vol. 75, pp. 774–779.

Fraki, J., et al., "Human Skin Proteases," *Arch. Derm. Res.,* 1976, vol. 256, pp. 113–126.

Forster, "Nature and Origin of Proteases in the Immunologically Induced Inflammatory Reaction," *J. Dent. Res.,* 1972, vol. 51, pp. 257–263.

Gerschman, R., et al., "Effect of Various Substances on Survival times of Mice Exposed to Different High Oxygen Tensions," *Amer. J. Physiol.,* 1958, vol. 192, pp. 563–571.

Glinski, W., et al., "The Activity of Polymorphonuclear Leukocyte Neutral Proteinases and Their Inhibitors in Patients with Psoriasis Treated with a Continuous Peritoneal Dialysis," *J. Investigative Dermatology,* 1980, vol. 75, No. 6, pp. 481–487.

Grando, et al., "Cytotoxic proteases in blister fluid of pemphigus and pemphigoid patients," *Int. J. Tissue React.* 1989, vol. 11, pp. 195–201.

Grando, et al., "Mediators of Inflammation in Blister Fluids From Patients With *Pemphigus vulgaris* and *Bullous pemphigoid,*" *Arch. Dermatol.,* 1989, vol. 125, pp. 925–930.

Hong, C., et al., "Synthesis and Antitumor Activity of 1–β–D–Arabinofuranosylcytosine Conjugates of Optical Isomers of Ether and Thioether Lipids," *Lipids,* 1993, vol. 28, No. 11, pp. 1021–1026.

Iriuchijima, S., et al., "Organic Synthesis by the Pummerer Reaction. II. Synthesis of α–Hydroxy Acid Derivatives from β–Keto Sulfoxides," *J. Am. Chem. Soc.,* 1975, p. 97:596.

Janoff, A., et al., "Proteases, Antiproteases, and Oxidants: Pathways of Tissue Injury During Inflammation," *Monogr. Pathol.,* 1982, vol. 23, pp. 62–82.

Jordon, R.E., "Pemphigus," *Dermatology in General Medicine,* McGraw Hill Book Co., 3rd ed., 1987, vol. 1, pp. 575–586.

Kikuchi, K., et al., "Metabolism and Penetration Through Blood–Brain Barrier of Parkinsonism–Related Compounds", *Drug Met. and Dispos.,* 1991, 19(1), p. 257.

Knight, MacPhadyen, Lepore, Kuwata, Eadie, O'Brien, "Enhancement of Ischaemic Rabbit Skin Flap Survival with the Antioxidant and Free–Radical Scavenger N–Acetylcysteine," *Clinical Sci.,* 1991, vol. 81, pp. 31–36.

Kohrt, A. et al., "Darstellung N–Geschutzer α–Aminodithiosaureester aus α–Aminonitrilen und α–Aminocarbonsauren," *Liebigs Ann. Chem.* 1992, pp. 595–605.

Lalitha, T., et al., "Effect of N–Acetyl–cysteine, D–Penicillamine and Buthionine Sulfoximine on Glutathione Levels and CNS Oxyten Toxicity in Rats," *Pharmacology and Toxicology,* 1990, vol. 66, pp. 56–61.

Lauharanta, Salonen and Vaheri, "Plasmin–like Proteinase Associated With High Molecular Weight Complexes in Blister Fluid of *Bullous pemphigoid,*" *Acta Derm. Venereol.* 1989, vol. 69, pp. 527–529.

Lemp and Roddy, "The Effect of Acetylcysteine (Mucomyst) on Reepithelialization of the Cornea," *Ann. Ophthalmol.* 1974, vol. 6, pp. 893–895.

Lever, W.F., "Pemphigus and Pemphigoid," *J. Am. Acad. Dermatol.,* 1979, vol. 1, pp. 2–31.

Lightowler and Lightowler, "Comparative Mucolytic Studies on Dithiothreitol, N–Acetylcysteine and L–Cysteine on Human Respiratory Mucus in vitro and their Effects on the Rate of flow of Mucus in the Exposed Trachea of the Rat on Topical Application," *Arch. Int. Pharmacodyn.* 1971, vol. 189, pp. 53–58.

Milligan, J.F., et al., "Current Concepts in Antisense Drug Design,"0 *J. Med. Chem.,* 1993, vol. 36, pp. 1923–1937.

Morioka, Naito and Ogawa,"The Pathogenic Role of Pemphigus Antibodies and Proteinase in Epidermal Acantholysis, " *J. Invest. Dermatol.,* 1981, vol. 76, pp. 337–341.

Morrison, Burnett and Stockley, "The Effect of Reducing Agents on Proteolytic Enzymes and Oxidation of $\alpha_1$–Proteinase Inhibitor,"0 *Biol. Chem. Hoppe Seyler,* 1986, vol. 367, pp. 117–182.

Naito, Morioka, Nakajima,Ogawa, "Proteinase Inhibitors Block Formation of Pemphigus Acantholysis in Experimental Models of Neonatal Mice and Skin Explants: Effects of Synthetic and Plasma Proteinase Inhibitors on Pemphigus Acantholysis," *J. Invest. Dermatol.,* 1989, vol. 93, 173–177.

Ogino, K., et al., "Biochemical Reactions Involving Thioesters," *Organic Sulfur Chemistry: Biochemical Aspects Oae,* S. and Okuyama, eds., CRC Press, Boca Raton, Florida, 1992, pp. 71–136.

Ohtani, O., et al., "Biochemical Properties of Thiol Proteinase Inhibitor Purified from Psoriatic Scales," 1982, vol. 78, No.4, pp. 280–284.

Peristeris, Platon, et al., "N–Acetylcysteine and Glutathione as Inhibitors of Tumor Necrosis Factor Production," *Cellular Immunology,* 1992, pp. 390–399.

Petroutsos, G., et al., "Effect of Acetycysteine (Mucomyst) on Epithelial Wound Healing," *Ophthalmic Res.* 1982 vol. 14, pp. 241–248.

Richaud, C., et al., "Directed Evolution of Biosynthetic Pathways," *J. Biological Chemistry* 1993, vol. 268, No. 36, pp. 2682–26835.

Sanders, A.P., et al., "Protection Against the Chronic Effects of Hyperbaric Oxygen Toxicity by Succinate and Reduced Glutathione," *Aerospace Med.,* 1972, vol. 43, pp. 533–536.

Senaldi, G., et al., "Protective Effect of N–Acetycysteine in Hapten–Induced Irritant and Contact Hypersensitivity Reactions," *J. Invest. Derm.,* Jun. 1994, vol. 102, No. 6, pp. 934–937.

Sharpe, R.J., "Pemphigus," *Manual of Clinical Problems in Dermatology,* Olbricht, Bigby and Arndt, eds., 1992, pp. 56–60.

Singer, Sawka, Samowitz and Lazarus, "Proteinase Activation: A Mechanism for Cellular Dyshesion in Pemphigus," *J. Invest. Dermatol.* 1980, vol. 74, pp. 363–367.

Singer, Hashimoto and Lazarus, "Antibody–Induced Proteinase Activation: A Proposed Mechanism for Pemphigus," *Springer Seminars in Immunopathology,* 1981, vol. 4, pp. 17–32.

Smilkstein, Knapp, Kulig and Rumack, "Efficacy of Oral N–Acetylcysteine in the Treatment of Acetaminophen Overdose," *N. Engl. J. Med.,* 1988, vol. 319, pp. 1557–1562.

Stanley, J.R. et al., "Pemphigus Antibodies Identify a Cell Surface Glycoprotein Synthesized by Human and Mouse Keratinocytes," *J. Clinical Investigation,* 1982, vol. 70, pp. 281–288.

Steinert, P.M., et al., "Characterization of a Class of Cationic Proteins that Specifically Interact with Intermediate Filaments," *Proc. Natl. Science*, 1981, vol. 78, No. 7, pp. 4097–4101.

Sun, T., et al., "Keratin Filaments of Cultured Human Epidermal Cells," *J. Biol. Chem.*, 1978, vol. 253, No. 6, pp. 2053–2060.

Sun, T., et al., "Differentiation of the Epidermal Keratinocyte in Cell Culture: Formation of the Cornified Envelope," *Cell*, vol. 9, pp. 511–521.

Takahashi, Patel, Labib, Diaz, Anhalt, "Experimentally Induced *Pemphigus vulgaris* in Neonatal BALB/c Mice: A Time–Course Study of Clinical, Immunologic, Ultrastructural, and Cytochemnical Changes,"0 *J. Invest. Dermatol.*, 1985, vol. 84, pp. 41–46.

Uhlmann, "Antisense Oligonucleotides: A New Therapeutic Approach," *Chemical Reviews*, 90(4), Jun. 1990.

Van Scott, E.J., et al., "Hyperkeratinization, Corneocyte Cohesion, and Alpha Hydroxy Acids," *J. American Academy of Dermatology*, 1984, vol. 11, No. 5, Part 1, pp. 867–879.

METHOD FOR TREATING DISEASES MEDIATED BY PROTEASES

This application claims is a continuation-in-part of U.S. Ser. No. 08/079,645, entitled "Method for Treating Diseases Mediated by Proteases," filed on Jun. 18, 1993 now abandoned.

This invention is a method for the treatment of diseases mediated by proteases that includes the topical or systemic administration of an effective amount of N-acetylcysteine or a derivative or salt thereof.

BACKGROUND OF THE INVENTION

There are a number of diseases that affect the skin and mucosal membranes which have been found to be mediated by proteases. Examples of protease mediated disorders include lichen planus, canker sores (aphthous ulcers), and a number of bullous diseases, including but not limited to pemphigus, bullous pemphigoid and cicatricial pemphigoid.

Lichen Planus

Lichen planus is a relatively common disease that results in cutaneous lesions and often oral lesions. Its prevalence averages between 0.5 and 1.0 percent in patients in large dental clinics (Arndt, K., in Fitzpatrick, Eisen, Wolff, Freedberg and Austen, *Dermatology in General Medicine*, 1987, Vol. 1, McGraw-Hill, Inc., New York, pp. 967–973). The disease occurs primarily after the age of 20, with most cases presenting in 40 to 60 year old patients (Arndt, K. in Fitzpatrick, Eisen, Wolff, Freedberg and Austen, *Dermatology in General Medicine*, 1987, Vol. 1, McGraw-Hill, Inc., New York, pp. 967–973).

Although squamous cell carcinoma can arise in lesions of chronic oral lichen planus, lichen planus is often self-limiting and requires treatment only if it is symptomatic (Bleicher, P. A. in *Manual of Clinical Problems in Dermatology*, Olbricht, Bigby and Arndt, eds., 1992, Little, Brown & Co., Boston, pp. 85–89). In certain instances, however, lichen planus results in significant morbidity, and in the case of severe or chronic lesions involving mucosal surfaces, potentially debilitating pain. Ulcerating lesions can be very persistent, sometimes lasting months or years.

Systemic corticosteroid therapy may be of some benefit for the treatment of lichen planus (Arndt, K. in Fitzpatrick, Eisen, Wolff, Freedberg and Austen, *Dermatology in General Medicine*, 1987, Vol. 1, McGraw-Hill, Inc., New York, pp. 967–73). The most reliable method of treating ulcerative lichen planus symptoms is with intra-lesional steroid injections, which is often repeated at frequent intervals. Potent topical steroids such as beta-methasone dipropionate and clobestol propionate are also be helpful, but the medication must be applied very frequently (every hour or so). Topical tretinoin, cyclosporine, and systemic antifungal agents, such as griseofulvin, have been reported to be somewhat effective in treating severely symptomatic oral lichen planus. No large, well designed studies, however, have proven the efficacy of these therapies. The use of potent topical steroids, particularly on mucosal surfaces, can result in dangerous side effects.

Bullous Diseases

A number of the protease mediated diseases are classified as bullous disorders. Bullae, more commonly known as blisters, are circumscribed, fluid containing elevated lesions which are usually more than 5 mm in diameter. Diseases exhibiting bullae can affect the skin or the mucous membranes. These diseases are very debilitating and potentially fatal. Patients can succumb to fluid or electrolyte imbalance or infection if serious bullous disease is not adequately treated. Bullous diseases include, but are not limited to, pemphigus, bullous pemphigoid, and cicatricial pemphigoid. These three typical examples of bullous conditions are briefly described below.

Pemphigus

Pemphigus is an auto-immune disease of the skin which is manifested by the loss of intercellular adhesion between the keratinocytes (cells) of the epidermis, resulting in bulla (blister) formation (Sharpe, R. J. in *Manual of Clinical Problems in Dermatology*, Olbricht, Bigby and Arndt eds., Little Brown & Co., Boston, 1992, pp. 56–60). Pemphigus can be further categorized by the specific site of the blisters in the various layers of the epidermis. *Pemphigus vulgaris* and *Pemphigus vegetans* exhibit blisters above the basal layer of the skin (i.e., the first layer of keratinocytes in the epidermis). In *Pemphigus foliaceus* and *Pemphigus erythematosus*, blister formation occurs just below the stratum corneum (i.e., higher in the epidermis).

*Pemphigus vulgaris* can affect all age groups. Lesions usually occur in the mouth, as well as on the chest, scalp, periumbilical, and intertriginous areas of the skin. Oral lesions frequently occur and may be the sole manifestation of the disease. This form of the disease can involve the oropharynx and other mucosal surfaces, sometimes extending into the esophagus and cardia of the stomach. *Pemphigus vulgaris* is characterized by intra-epidermal blister formations due to acantholysis (i.e., loss of intercellular adhesions) in the superbasilar epidermis and intact basal cells that histologically resemble a row of tombstones at the base of the blister.

*Pemphigus vegetans* is clinically manifested by vegetating legions and sometimes by pustules. The latter may represent super-infection at the edges of the broken bullae. Intertriginous regions are more commonly affected. The histology of this form commonly shows abscess formation within the epidermis. Eosinophils are present in moderate numbers. Hyperkeratosis, pseudoepitheliomatous hyperplasia, and papillomatosis also occurs.

The blisters formed in *Pemphigus foliaceus* are superficial and easily ruptured. Primary symptoms often include crusting, scales, erosion, and excoriations.

*Pemphigus erythematosus* is similar to *Pemphigus foliaceus* histologically, and represents a localized form of pemphigus. Lesions of this type are characterized by a lupus-like butterfly rash as well as bullous and seborrheic dermatitis-like lesions. This type of pemphigus can be associated with other auto-immune diseases including rheumatoid arthritis, thymoma, myasthenia gravis and systemic lupus erythematosus.

Because of the severity of symptoms and the high morbidity and mortality associated with pemphigus, hospitalization is often necessary. Untreated or unresponsive pemphigus patients can develop sepsis, cachexia, and major fluid and electrolyte imbalances similar to those observed in burn patients.

Current treatment of pemphigus involves the use of corticosteroids, including high dosages of oral prednisone or prednisolone. Accordingly, these patients must be closely monitored for adrenocorticoid side effects. It has also been reported that immunosuppressive agents such as cyclophosphamide, azathioprine, methotrexate and cyclosporine-A, or a combination of immunosuppressive agents with high doses of prednisone may be useful in the symptomatic treatment of pemphigus (Lever, *J. Am. Acad. Dermatol.* 1979, Vol. 1, pp. 2–31). As with treatment with prednisone or prednisolone alone, patients undergoing immunosuppressive treatment must be closely monitored for adverse side effects. Treatment of pemphigus with gold compounds alone or in combination with prednisone has also been reported (Lever, *J. Am. Acad. Dermatol.* 1979, Vol. 1, pp. 2–31).

Bullous Pemphigoid

Bullous pemphigoid is the most common bullous disease of the skin. It is more prevalent in elderly patients than in younger patients. Clinical signs frequently include large tense blisters, on erythematous or non-erythematous skin or on urticarial plaques. Bullae often occur on the joints of the extremities, lower abdomen, groin, and inner thighs. The blisters do not rupture easily; after they rupture, however, the lesions usually heal without scarring. A mortality rate of 10 to 20 percent is reported for the disease, largely due to side-effects from the use of systemic steroid therapy.

As with pemphigus, treatments for the various forms of bullous pemphigoid include systemic glucocorticosteroids. Often treatment will include an immuno-suppressive agent in addition to the steroids. Intra-lesional steroids may be beneficial in preventing scarring and may be used to treat mucous membrane disease. Topical treatments including steroid creams and Burows' solution baths are used to prevent secondary infection and scarring.

Cicatricial Pemphigoid

Cicatricial pemphigoid, also called benign mucous membrane pemphigoid or ocular pemphigoid, is an uncommon chronic subepidermal bullous dermatosis which involves primarily the mucous membranes (Baden, L. A., *Manual of Clinical Problems in Dermatology*, Little, Brown & Co., Boston, 1992, pp. 54). Its chronic lesions often cause scarring. It frequently leads to blindness in the case of the ocular lesions. Oral and ocular membranes are frequently involved, but other mucous membranes including the nasal mucosa, pharynx, larynx, esophagus, genitalia, anus, and the skin may also be affected. In many patients the disease begins with desquamative gingivitis (loss of the surface of the gums), with fragility, pain, and easy bleeding of the gingivae.

Current treatments for this disorder are less than satisfactory (see Bleicher, supra; Arndt, K. in Fitzpatrick, Eisen, Wolff, Freedberg and Austen, *Dermatology in General Medicine*, 1987, Vol. 1, McGraw-Hill, Inc., New York, pp. 582–584). As with pemphigus, treatment of cicatricial pemphigoid often requires high doses of systemic corticosteroids and immunosuppressive agents. Because of the scarring associated with cicatricial pemphigoid, long term systemic steroids have been used in these patients despite the side effects. Cyclophosphamide, methotrexate, dapsone and azathioprine have been beneficial to some patients, while others have shown little improvement with these agents. Topical and intra-lesional steroids seem to be less effective in cicatricial pemphigoid than in oral lichen planus.

A common feature of lichen planus, pemphigus, bullous pemphigoid, cicatricial pemphigoid and lichen planus is the role of proteases in their pathogenesis. For example, in one study, cytotoxic proteases were identified in the blister fluid of pemphigus and pemphigoid patients (Grando, Glukhenky, Drannik, Kostromin and Chernyavsky, *Int. J. Tissue React.* 1989, Vol. 11, pp. 195–201). Similar observations have been reported by other investigators (Lauharanta, Salonen and Vaheri, *Acta Derm. Venereol.* 1989, Vol. 69, pp. 527–9; Morioka, Naito and Ogawa *J. Invest. Dermatol.* 1981, Vol. 76, pp. 337–41; Singer, Sawka, Samowitz and Lazarus, *J. Invest. Dermatol.* 1980, Vol. 74, pp. 363–7). Inflammatory responses, such as those seen in lichen planus, result in the local production and/or elaboration of proteases and tissue injury at the disease site. (Barnhart, Quintana, Lenon, Bluhm and Riddle, *Ann. N.Y. Acad. Sci.* 1968, Vol. 146, pp. 527–39; Janoff and Carp, *Monogr. Pathol.* 1982, Vol. 23, pp. 62–82; Grando, Glukhenky, Drannik, Epshein, Kostromin and Korostash, *Arch. Dermatol.* 1989, Vol. 125, pp. 925–30; Forster, *J. Dent. Res.* 1972, Vol. 51, pp. 257–63). Finally, in the case of pemphigus, there is evidence that direct induction of proteinase activity by autoantibodies significantly contributes to the pathogenesis of the disease (Singer, Hashimoto and Lazarus, *Springer Semin. Immunopathol.* 1981, Vol. 4, pp. 17–32).

The protease inhibitors ω-guanidino ester gabexate mesylate, camostat mesylate and nafomastat mesylate inhibit the induction of acantholysis in an organ culture system, but have little or no effect on lesion formation in a neonatal mouse model of pemhigus (Naito, Morioka, Nakajima, Ogbawa, *J. Invest. Dermatol.*, 1989, Vol. 93 pp. 173–77). By contrast, the natural plasma proteinase inhibitor, alpha-1-proteinase inhibitor, completely inhibited acantholysis formation in the mouse model. Based on this work, it appears that only certain proteinase inhibitors are effective in the treatment of pemphigus.

Canker Sores (Aphthous Ulcers)

Aphthous ulcers are inflammatory lesions of unknown etiology that can effect any mucosal surface, but occur most often in the mouth (Cropley, T. G. in *Manual of Clinical Problems in Dermatology*, Olbricht, S. M., Bigby, M. E., Arndt, K. A., eds. Little, Brown, and Co. Boston, 1992, pp. 312). The presence of an extensive inflammatory infiltrate in these lesions often result in tissue injury, which reflects the actions of a host of soluble mediators such as proteases and tumor necrosis factor. Current treatments include hygienic measures, topical anesthetics and various unproven therapies such as oral suspensions of tetracyclines and systemic and topical corticosteroids. Patients are frequently instructed to avoid trauma to the oral cavity (such as sharp bread crusts or hard toothbrushes) which may precipitate new ulcers.

In light of the seriousness of the symptoms associated with the disorders described above, there clearly remains a need for effective, safe topical and systemic methods for their treatment.

Therefore, it is an object of the present invention to provide a method for the topical treatment of disorders mediated by proteases.

It is another object of the present invention to provide a method for the systemic treatment of the disorders mediated by proteases.

SUMMARY OF THE INVENTION

A method for the topical or systemic treatment of disorders mediated by proteases that cause skin or mucosal lesions, and in particular, pemphigus, cicatricial pemphigoid, bullous pemphigoid, lichen planus, and canker sores (aphthous ulcers), is disclosed wherein the host is treated with an effective amount of N-acetylcysteine ("NAC") or a derivative thereof, or its pharmaceutically acceptable salt, optionally in a pharmaceutically acceptable diluent or carrier for systemic or topical delivery. The active compound or its derivative is administered for a sufficient time period to alleviate the undesired symptoms and or the clinical signs associated with the disorder.

Oral lesions associated with these disorders can be treated, for example, with an mouthwash rinse that contains an effective amount of N-acetylcysteine or its derivative or salt. The mouthwash is used as often as necessary to obtain amelioration of symptoms, and typically from one to several times a day until the desired benefit is achieved. The rinse is swished and expectorated or swallowed by the patient. When treating lesions of the oral mucosa, the taste and odor of NAC can be masked with an additive such as lemon or peppermint oil.

Skin or mucosal lesions on non-oral membranes (for example, ocular, vaginal, nasal, or oral membranes) can be treated with an effective amount of N-acetylcysteine in a carrier for topical delivery. The active compound is administered in an effective dosage range to cause suppression of the symptoms. In one embodiment, a wet gauze compress soaked with a solution of N-acetylcysteine or its derivative or salt is maintained on the lesion for a period of time, from one to several times a day. In another embodiment, an effective amount of N-acetylcysteine or its derivative or salt is applied to the lesion in a cream, gel, ointment, diluent, foam or paste, from one to several times a day.

In an alternative embodiment, a method for the treatment of disorders mediated by proteases is provided that includes administering an effective amount of N-acetylcysteine, or its derivative or pharmaceutically acceptable salt thereof, in a carrier for systemically delivery.

NAC or its derivative or salt can be useful in interrupting the cascade of events which result in pathological tissue injury and thus should assist in accelerating the healing of painful lesions associated with aphthous ulcers and preventing the formation of new lesions.

DETAILED DESCRIPTION OF THE INVENTION

I. N-Acetylcysteine and its Derivatives

The term alkyl, as used herein, refers to a saturated straight, branched, or cyclic (or a combination thereof) hydrocarbon of $C_1$ to $C_{22}$, and specifically includes methyl, ethyl, propyl, isopropyl, cyclopropylmethyl, cyclobutylmethyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term aryl, as used herein, refers to phenyl, or substituted phenyl, wherein the substituent is halo, alkyl, alkoxy, alkylthio, haloalkyl, hydroxyalkyl, alkoxyalkyl, methylenedioxy, cyano, C(O)(alkyl), carboxylic acid, $CO_2$alkyl, amide, amino, alkylamino or dialkylamino, and wherein the aryl group can have up to 3 substituents.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

As used herein the term fatty acid refers to a long chain ($C_6$ to $C_{22}$) aliphatic carboxylic acid The term "enantiomerically enriched composition or compound" refers to a composition or compound that includes at least 95% by weight of a single enantiomer of the compound.

The term inorganic cation refers to a charged moiety in which an atom other than carbon carries a positive charge, and includes, but is not limited to, $H^+$, potassium, sodium, ammonium, mono, di, or trialkylammonium, quaternary amine, specifically including but not limited to the quaternary ammonium salt of the formula $NR_4^{+Z-}$, wherein R is independently alkyl or benzyl and Z is a counteranion, including chloride, bromide, iodide, —O-alkyl, tolunesulfonate, methylsulfonate, sulfonate, phosphate, or carboxylate (such as benzoate, succinate, acetate, glycolate, succinate, maleate, malate, citrate, tartrate, ascorbate, benzoate, cinnamoate, mandeloate, benzyloate, and diphylacetate); or a multivalent ion such as calcium, barium, aluminum, or magnesium, zinc, bismuth, copper, cobalt, nickel, cadmium, and the like, or a cation of a nitrogenous base including but not limited to N,N-dibenzylethylenediamine, D-glucosamine, or ethylenediamine.

As used herein, the term pharmaceutically acceptable derivative of N-acetylcysteine refers to either:

(i) any compound that upon administration to the recipient, is capable of providing directly or indirectly, the compounds disclosed herein; including, or alternatively, (ii) a compound of the formula:

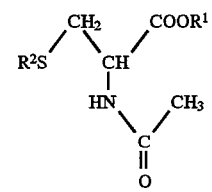

wherein $R^1$ is H, alkyl, aryl, alkaryl, aralkyl, alkyloxyalkyl including methoxymethyl, aryloxyalkyl such as phenoxymethyl, an amino acid salt formed by the reaction of the amino group of a naturally occurring amino acid with the carboxylic acid group of the N-acetylcysteine or derivative thereof; an amine salt formed by the reaction of an amine-containing antibiotic with the carboxylic acid group of the N-acetylcysteine, or an inorganic cation; and wherein the term amino acid includes but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl; and $R^2$ is H, alkyl, aryl, alkaryl, aralkyl, alkyloxyalkyl including methoxymethyl, aryloxyalkyl such as phenoxymethyl, C(O or S)alkyl, C(O or S)aryl, C(O or S)alkaryl, C(O or S)aralkyl, C(O or S)alkyloxyalkyl, C(O or S)acyloxyalkyl, or phosphate. $R^2$ can also be the residue of a saturated or unsaturated fatty acid, including but not limited to lauric, oleic, caproic, linoleic, linolenic, caprylic, capric, perlargonic, neononanoic, neodecanoic, palmitelaidoic, myristic, palmitic, stearic, arachidic, behenic, lignoceric, heptanoic, nonanoic, undecanoic, tridecanoic, pentadecanoic, heptadecanoic, nonadecanoic, heneicosanoic, tricosanoic, arachidonic, docosahexanoic, elaidic, erucic, nervonic, palmitoleic or petriselinic acid. Alternatively, $R^2$ can be the residue of lactic acid, retinoic acid, or ascorbic acid (to form the thioester), or other α-hydroxy acid, or the residue of a dicarboxylic acid (wherein N-acetylcysteine is bound through either or both carboxylic acid groups), including but not limited to cromolyn, nedocrimil, or other mast cell stabilizers, azelaic acid, or methotrexate. In yet another embodiment, $R^2$ is the residue of sebacic acid, phthalic acid, terephthalic acid, isophthalic acid, adipic acid, 1,10-dodecanoic acid, bis(p-carboxyphenoxyalkane), fumaric acid, 1,4-diphenylenediacrylic acid, branched monomers such as 1,3,5-benzenetricarboxylic acid, azeleic acid, pimelic acid, suberic acid (octanedioic acid), itaconic acid, biphenyl-4,4'-dicarboxylic acid, and benzophenone-4,4'-dicarboxylic acid, p-carboxyphenoxyalkanoic acid, hydroquinone-O,O-diacetic acid, 1,4-bis-carboxymethyl benzene, 2,2-bis-(4-hydroxyphenyl) propane-O,O-diacetic acid, 1,4-phenylene-dipropionic acid, and cyclohexane dicarboxylic acid (wherein N-acetylcysteine is bound through one or more carboxylic acid groups to form thioesters). In one embodiment, at least one of $R^1$ or $R^2$ is not hydrogen.

Non-limiting examples of amine-containing antibiotics that can be used to form a salt with N-acetylcysteine include, but are not limited to, erythromycin, propionylerythromycin, neomycin, gentomycin, mechlocyclin, tobramycin, and kanamycin.

In another embodiment, a dimer or oligomer of NAC or its derivative is provided. The dimer can be formed by joining two —$SR^2$ moieties to form a disulfide bridge (with the elimination of the $R^2$ groups), or by joining two carboxylate moieties to form an anhydride. Alternatively, the dimer can be formed by combining an —$SR_2$ moiety of NAC or its derivative with a $CO_2R^1$ moiety of another NAC molecule or derivative to form a thioester dimer. In another embodiment, two or more NAC molecules or derivatives are combined through thioester linkages.

It has been discovered that disorders mediated by proteases can be treated by the topical or systemic administration of an effective amount of N-acetylcysteine, or a derivative thereof, or a pharmaceutically acceptable salt of N-acetylcysteine or a derivative thereof, optionally in a pharmaceutical carrier for topical or systemic delivery.

Cysteine is an amino acid with one chiral carbon atom. It exists as an L-enantiomer, a D-enantiomer, or a racemic mixture of the L and D enantiomers. The L-enantiomer is the naturally occurring configuration.

N-acetylcysteine (acetamido-mercaptopropionic acid, NAC) is the N-acetylated derivative of cysteine, as illustrated below. It also exists as an L-enantiomer, a D-enantiomer, or a racemic mixture of the L and D enantiomers. Any of these three forms of NAC can be used in the treatment of disorders mediated by proteases described herein. In a preferred embodiment, an enantiomerically enriched composition of NAC or its salt or derivative, and most preferably, the N-acetylated derivative of the naturally occurring L-enantiomer, is used in the treatment process.

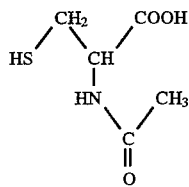

NAC is known to be an effective mucolytic agent (Lightowler and Lightowler, *Arch. Int. Pharmacodyn.* 1971, Vol. 189, pp. 53–8) whose pharmacology is related to the reactive sulfhydryl group in the molecule. The sulfhydryl group probably opens sulfide linkages in mucus, thereby lowering mucosal viscosity. NAC is also used for the treatment of acetaminophen overdoses (Smilkstein, Knapp, Kulig and Rumack, *N. Engl. J. Med.* 1988, Vol. 319, pp. 1557–62). A large overdose of acetaminophen results in a larger portion of the drug being metabolized via a free radical (cytochrome P-450) pathway which results in hepatic cellular necrosis. N-acetylcysteine, when administered within the first few hours of overdose, protects the liver by acting as an alternate substrate for conjugation with and detoxification of the reactive metabolite.

In addition to its mucolytic and free radical scavenging ability, NAC has been reported to be an effective collagenase inhibitor (Lemp and Roddy, *Ann. Ophthalmol.* 1974, Vol. 6, pp. 893–5) and an antioxidant in vivo (Knight, MacPhadyen, Lepore, Kuwata, Eadie, O'Brien, *Clinical Sci.*, 1991, Vol. 81, pp. 31–36; Ellis, Dodson, Police, *J. Neurosurg.*, 1991, Vol. 75, pp. 774–79). It has also been reported that NAC reduces the activity of the proteolytic porcine enzymes leukocyte elastase and pancreatic elastase by greater than 55% in vitro (Morrison, Burnett and Stockley, *Biol. Chem. Hoppe Seyler* 1986, Vol. 367, pp. 177– 82). Given the complexity of disorders such as pemphigus, cicatricial pemphigoid, bullous pemphigoid, lichen planus, and canker sores, one could not predict from this report whether NAC would be an effective treatment in vivo for these diseases.

II. Pharmaceutical Compositions of NAC

Humans, equine, canine, bovine, feline and other animals, and in particular, mammals, suffering from diseases mediated by proteases, can be treated by administering to the patient or animal an effective amount of NAC or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Pharmaceutically acceptable carboxylic acid and mercaptyl salts are known to those skilled in the art, including inorganic salts with cations such as zinc, calcium, bismuth, barium, magnesium, aluminum, copper, cobalt, nickel, cadmium, sodium, potassium, and the like, or with a cation formed with a nitrogenous base such as ammonia, N,N-dibenzylethylene-diamine, D-glucosamine, or ethylenediamine.

In general, the derivatives of N-acetylcysteine disclosed herein are "prodrugs" of N-acetylcysteine, that are either active in the prodrug form or are cleaved in vivo to the parent, active compound. Modifications of the active compound can affect the bioavailability and rate of metabolism of the active species, thus providing control over the delivery of the active species. For example, it is well known in the art that various modifications of the active molecule, such as alteration of charge, can effect water and lipid solubility and thus alter the potential for percutaneous absorption. For example, increasing the lipophilicity of NAC by formation of the thioester with a long chain fatty acid will enhance its ability to cross certain biological membranes (i.e., skin, mucous membranes, ocular membranes, and the blood brain barrier). Further, the modifications can affect the bioactivity of the compound, in some cases increasing the activity over the parent compound. This can easily be assessed by preparing the derivative and testing its activity according to the methods described herein, or other method known to those skilled in the art.

N-acetylcysteine or its derivative or salt is preferably applied in the form of a topical composition. The composition can be formulated in a variety of ways known to those skilled in the art, for example, in a solid form such as a powder; a liquid form such as a solution or a suspension in an aqueous or oily medium; or a semi-liquid formulations such as a cream, jelly, paste, ointment, or salve. In one embodiment, the compound is applied in the form of a solution, gel, ointment, cream, lotion or foam, in a 1–100%, for example a 10–20% by weight, aqueous solution. Acetylcysteine is currently available in 10 and 20% aqueous solutions (Mucomyst, Mucosil). In another embodiment, the active ingredient or its derivative or salt or composition thereof is incorporated into a lesion cover such as a plaster, bandage, dressing, gauze pad or the like. Alternatively, the active ingredient or its derivative or salt or composition thereof can be administered by transdermal patch.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; anti-bacterial agents such as benzyl alcohol or methyl parabens; anti-oxidants such as ascorbic acid, BHA or BHT, or sodium bisulfite; chelating agents such as ethylenediaminetetraacetic acid; buffers such as acetates, citrates or phosphates and agents for the adjustment of tonicity such as sodium chloride or dextrose.

The vehicle, or carrier, can be modified to enhance cutaneous absorption, enhance the reservoir effect, or minimize potential irritancy or neuropharmacological effects of the composition. Examples of penetration enhancers include N-methylpyrrolidine and SEPAs (1,3-dioxolanes). SEPAs are available from MacroChem Corporation and are described in U.S. Pat. No. 4,861,764 and European Pat. No. 0 268 460. These enhancers are designed to assist in the penetration of drugs into the skin. For other examples, see, in general, Arndt, K. A., Mendenhall, P. V., "The Pharmacology of Topical Therapy", *Dermatology in General Medicine*, 1987; Fitzpatrick, Eisen, Wolff, Freeberg, Austen, eds., 3d ed., McGraw Hill, Inc., New York, pp. 2532–2540.

The active compound is included in the pharmaceutically acceptable carrier or diluent in an amount sufficient to deliver to a host a therapeutically effective amount of the drug without causing serious toxic effects in the patient treated. A typical topical dosage will range from 1 to 30 weight percent in a suitable carrier. A preferred systemic dose of the active compound for all of the above-mentioned conditions is in the range from about 10 to 8000 mg/kg, preferably 100 to 1500 mg/kg per day, more generally 300 to about 1200 mg per kilogram body weight of the recipient per day. The effective dosage range of the pharmaceutically acceptable derivatives and salts thereof can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to pills, tablets, troches, and caplets containing 250 to 3000 mg, preferably 500 to 3000 mg of active ingredient per unit dosage form. A oral dosage of 750 to 1500 mg is usually convenient.

The active ingredient can be administered by the intravenous injection of a solution or formulation of the active ingredient, optionally in physiological saline or phosphate buffered saline (PBS), or an aqueous medium or administered as a bolus of the active ingredient.

The concentration of active compound in the drug composition will depend on absorption, distribution, deactivation, and excretion rates of the drug as well as other factors known to those of skill in the art. Dosage values will also vary with the severity of the condition to be alleviated. For any particular subject, specific dosage regimens should be adjusted over time according to the individual need and the professional judgment of the person administering or supervising the administration of the compositions. The concentration ranges set forth herein are exemplary only and are not intended to limit the scope or practice of the claimed composition. The active ingredient can be administered at once, or can be divided into a number of smaller doses to be administered at varying time intervals.

Natural or artificial flavorings or sweeteners can be used to enhance the taste and odor of topical preparations applied for local effect to mucosal surfaces. Inert dyes or colors can also be added, particularly for compositions designed for application to oral and mucosal surfaces.

Oral compositions will generally include an inert diluent or an edible carrier. They may be enclosed in gelatin capsules or compressed into tablets. For the purpose of oral therapeutic administration, the active compound can be used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose, saccharin or Nutrasweet (phenylalanine); a flavoring agent such as peppermint, lemon, cinnamon, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose, Nutrasweet (phenylalanine) or saccharrin as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, anti-fungals, anti-inflammatories, disinfectants, or anti-viral compounds.

In one embodiment, the active compounds are prepared with carriers that will protect the compound against rapid elimination from the body, such as a controlled release formulation, including implants and microencapsulated delivery systems. Biodegradable, biocompatible polymers can be used, such as poly(ethylene vinyl acetate), polyanhydrides, poly(glycolic acid), collagen, polyorthoesters, and poly(lactic acid). Methods for preparation of such formulations will be apparent to those skilled in the art. The materials can also be obtained commercially from Alza Corporation and Nova Pharmaceuticals, Inc.

III. Methods for the Evaluation of Effectiveness of NAC in the Treatment of Pemphigus in Model Systems The effectiveness of N-acetylcysteine or its derivative or salt in the treatment of any of the forms of pemphigus described above can be evaluated by one or more of the following methods: (a) in an established organ culture model where the degree of acantholysis can be measured, after introduction of exogenous pemphigus antibody; (b) in a neonatal mouse model where disease can be induced, and evidence of clearing can be monitored; and or (c) in humans with pemphigus.

1. Experimental procedure for purification of pemphigus antibodies from human donors The pemphigus antibodies to be used in the analysis are purified and prepared in the following manner (Anhalt, Till, Diaz, Labib, Patel and Eaglstein, *J. Immunol.* 1986, Vol. 137, pp. 2835–40). Serum is obtained from human patients with the clinical, histologic and immunologic features of pemphigus. The IgG fractions of the sera are purified by 40% ammonium sulfate precipitation, followed by ion exchange chromatography. IgG fractions prepared in this manner are free of significant protease contamination when assayed. Further or alternate purification regimens can include protein-A or protein-G binding and elution, and various chromatography schemes that exploit differences in the size and charge of the IgG, as known to those skilled in the art. The fractions are concentrated and sterilized via filtration. The pemphigus anti-body titer in the serum is then measured.

2. Organ Culture Model for Pemphigus

Production of acantholysis in vitro can be carried out as follows (Lever, *J. Am. Acad. Dermatol.* 1979, Vol. 1, pp. 2–31). Normal human skin is maintained in organ cultures to which sera of patients with pemphigus is added. Direct IF staining of the explants with fluorescein-labeled goat anti-human IgG shows that, after incubation, binding of the pemphigus IgG has occurred in the intercellular cement substance of the epidermis. Suprabasal acantholysis is observed which progresses to extensive acantholysis. Complement is not required for the in vitro production of acantholysis since heating the pemphigus sera at 56° C. for thirty minutes does not prevent acantholysis (Lever, *J. Am. Acad. Dermatol.* 1979, Vol. 1, pp. 2–31).

The ability of NAC or its derivative or salt to lessen or eliminate acantholysis in vitro caused by exposure to pemphigus-IgG the following experiment can be evaluated as follows. Normal human skin is cultured according to the method described by Naito, et al., (Naito, Morioka, Nakajima, Ogawa, *J. Invest. Dermatol.* 1989, Vol. 93, 173–77). Skin is sliced into 2×2 mm pieces thick. The skin is then floated on top of a total volume of 1.0 mL culture medium with the assistance of paraffin edged lens paper. The cultures are kept in humid atmosphere containing $CO_2$ in air for 24, 48 and 72 hours. The culture medium should contain approximately 7 mg/mL of pemphigus IgG with or without the NAC or its derivatives or salts. After each culture period, the skin explants are examined by routine histologic (hemotoxylin and eosin staining) methods. The final concentration of NAC, its derivative, or its salt should range from 0.1 to 20 mg/mL. The skin can be preincubated (1–24 hours) with NAC, its derivative or salt prior to addition of pemphigus IgG. Acantholysis is evaluated on a scale of (–), (+), (++), or (+++), where (–) is no acantholysis, (+) is positive on 10–30%, (++) is positive on 30–70%, and (+++) is positive on 70–100% of the epidermis in the histologic section.

3. Neonatal Mouse Model for Pemphigus

The ability of NAC or its derivative or salt to reduce the symptoms of pemphigus in vivo can be evaluated in a neonatal mice model (Anhalt, Labib, Voorhees, Beals and Diaz, *N. Engl. J. Med.* 1982, Vol. 306, pp. 1189–96). Purified IgG fractions are injected i.p. into neonatal mice using a 30 gauge needle in a single administration of 10 mg IgG per gram body weight according to an established model (Takahashi, Patel, Labib, Diaz, Anhalt, *J. Invest. Dermatol.* 1985, Vol. 84, pp. 41–46). Skin and serum samples are obtained from animals receiving injections of either normal human IgG (control) or human pemphigus IgG. Skin samples from the flank region, where lesions most often occur are processed for direct immuno-fluorescence. Human pemphigus antibodies are also monitored in the animals' serum, to confirm transfer of the pemphigus antibodies. One group of mice is treated with topical administration of the test compound and monitored for disease improvement by sampling the skin and assessing its appearance by histology and/or by clinical appearance.

Specifically, within 30 minutes of pemphigus IgG injection, the neonatal mice receive injections of NAC, its salt, or its derivative prepared in PBS. The administered dosages of NAC, its derivative, or its salt range from 13 μg/g of mouse body weight to 2 mg/g mouse body weight. Each of the solutions to be injected are sterilized by filtration through an 0.45 μm millipore filter. Effects of inhibitors on epidermal acantholysis by pemphigus IgG in neonatal mice are evaluated visually (positive if the presence of Nikolsky sign is observed; i.e., apparently normal epidermis can be separated at the basal layer and rubbed off when pressed with a sliding motion on any part of the skin surface) as well as histologically (acantholytic changes are examined at five sites) 24 hours after pemphigus IgG is injected. To carry out biochemical analysis 24 hours after pemphigus IgG injection the mice are sacrificed and the whole skin of each animal removed. At least five different sites from each removed skin are then examined for histologic analysis.

In addition to acantholysis, the effect of NAC, its derivatives and its salts on the level of the protease, plasminogen activator, in the neonatal mouse epidermis is determined. Skin samples are removed as described above at 3 and 24 hours after injection of pemphigus IgG with preinjection of the test compound. The skin is isolated by heating the skin at 56° C. for 30 seconds and putting it through 2 freeze thaw cycles. It is then homogenized and spun at 4° C. for 2 hours in 0.01M sodium monophosphate, pH 7.0 and centrifuged at 750 g for 10 min. The pellet is extracted with 2M potassium thiocyanate (KSCN) with 0.01% Triton X-100 4° C. for 2 hours. The extracts are centrifuged at 750 g for 10 min, and the supernatant dialyzed against 0.12M glycine-NaOH, pH 8.5. Plasminogen activity is determined spectroscopically according to literature procedures (Naito, Morioka, Nakajima, Ogawa, H. *J Invest Dermatol,* 1989, vol. 93, 173–177).

IV. Methods for the Evaluation N-acetylcysteine in Humans with oral lesions

The effectiveness of treatment of patients with oral lesions resulting from lichen planus, bullous pemphigoid, cicatricial pemphigoid, pemphigus or canker sores (aphthous uclers) with NAC or its derivatives or salts thereof can be evaluated as described generally for treatment of lichen planus by Eisen, Ellis, Duell, Griffiths and Voorhees, in *N. Engl. J. Med.* 1990, Vol. 323, pp. 290–4. For example, patients with symptomatic oral lichen planus are given either placebo or a topical N-acetylcysteine solution, gel, or ointment containing 1 to 50% NAC or other test compound. The solutions are swished for several minutes and expectorated or swallowed several times daily.

Clinical evaluations are performed by the same physician for the duration of the experiment. Each patients disease is measured on a scale of 1 to 4, with 1 indicating minimal disease, and 4 indicating severe lesions. The degree of erosion, erythema, and reticulation of each lesion is separately scaled over time for a period ranging from 1 day to 6 months, as desired. In addition, the patients evaluate lesion discomfort on a scale of 1 to 4.

Analogously, diseases involving other mucosal membrane surfaces or the skin can be treated topically or systemically via oral or i.v. injection with N-acetylcysteine or its derivative or salt and the results compared with placebo.

Modifications and variations of the present invention relating to a method for the treatment of diseases mediated by proteases that includes the topical or systemic administration of an effective amount of N-acetylcysteine or a derivative or salt thereof will be obvious to those skilled in the art from the foregoing detailed description of the invention. Such modifications and variations are intended to fall within the scope of the appended claims.

We claim:

1. A method for the treatment of disorders mediated by proteases in mammals that result in skin or mucosal lesions selected from the group consisting of lichen planus, canker sores (aphthous ulcers), and bullous diseases, comprising:

topically applying to the skin or mucosal lesion an effective amount of N-acetylcysteine or a pharmaceutically acceptable salt thereof, optionally in a pharmaceutically acceptable carrier to topical administration.

2. A method for the treatment of disorders mediated by proteases in mammals that result in skin or mucosal lesions selected from the group consisting of lichen planus, canker sores (aphthous ulcers), and bullous diseases, comprising:

systemically administering to a mammal in need thereof an effective amount of N-acetylcysteine or a pharmaceutically acceptable carrier for systemic administration.

3. A method for the treatment of disorders mediated by proteases in mammals that result in skin or mucosal lesions selected from the group consisting of lichen planus, canker sores (aphthous ulcers), and bullous diseases, comprising:

topically applying to the skin or mucosal lesion an effective amount of a derivative of N-acetylcysteine of the formula $$\begin{array}{c} R^2S \diagup {}^{CH_2}\diagdown_{CH}\diagup{}^{COOR^1} \\ | \\ HN\diagdown_{\underset{\|}{C}}\diagup CH_3 \\ O \end{array}$$

wherein $R^1$ is H, alkyl, aryl, alkaryl, aralkyl, alkyloxyalkyl, aryloxyalkyl, an amino acid salt formed by the reaction of the amino group of a naturally occurring amino acid with the carboxylic acid group of the N-acetylcysteine, an amine salt formed by the reaction of an amine-containing antibiotic with the carboxylic acid group of the N-acetylcysteine, or an inorganic cation, and $R^2$ is H, alkyl, aryl, alkaryl, aralkyl, alkyloxyalkyl, aryloxyalkyl, C(O or S) alkyl, C(O or S) aryl, C(O or S) alkaryl, C(O or S) aralkyl, C(O or S) alkyloxyalkyl, C(O or S) acyloxyalkyl, phosphate, or an inorganic cation; the residue of a saturated or unsaturated fatty acid; the residue of lactic acid, retinoic acid, or ascorbic acid; or the residue of an alkyl or aromatic dicarboxylic acid;

or a pharmaceutically acceptable salt thereof, optionally in a pharmaceutically acceptable carrier for topical administration.

4. A method for the treatment of disorders mediated by proteases in mammals that result in skin or mucosal lesions selected from the group consisting of lichen planus, canker sores (aphthous ulcers), and bullous diseases, comprising:

systemically administering an effective amount of a derivative of N-acetylcysteine of the formula $$\begin{array}{c} R^2S \diagup {}^{CH_2}\diagdown_{CH}\diagup{}^{COOR^1} \\ | \\ HN\diagdown_{\underset{\|}{C}}\diagup CH_3 \\ O \end{array}$$

wherein $R^1$ is H, alkyl, aryl, alkaryl, aralkyl, alkyloxyalkyl, aryloxyalkyl, an amino acid salt formed by the reaction of the amino group of a naturally occurring amino acid with the carboxylic acid group of the N-acetylcysteine, an amine salt formed by the reaction of an amine-containing antibiotic with the carboxylic acid group of the N-acetylcysteine, or an inorganic cation, and $R^2$ is H, alkyl, aryl, alkaryl, aralkyl, alkyloxyalkyl, aryloxyalkyl, C(O or S) alkyl, C(O or S) aryl, C(O or S) alkaryl, C(O or S) aralkyl, C(O or S) alkyloxyalkyl, C(O or S) acyloxyalkyl, phosphate, or an inorganic cation; the residue of a saturated or unsaturated fatty acid; the residue of lactic acid, retinoic acid, or ascorbic acid; or the residue of an alkyl or aromatic dicarboxylic acid;

or a pharmaceutically acceptable salt thereof, optionally in a pharmaceutically acceptable carrier for systemic administration.

5. The method of claim 1 wherein the compound is applied in the form of a 10 or 20 percent aqueous solution.

6. The method of claim 3 wherein the compound is applied in the form of a 10 or 20 percent aqueous solution.

7. The method of claim 1 wherein the compound is applied in the form of a 1 to 100% topical solution, gel, ointment, cream, lotion or foam.

8. The method of claim 3 wherein the compound is applied in the form of a 1 to 100% topical solution, gel, ointment, cream, lotion or foam.

9. The method of claim 1 wherein the compound is applied several times a day.

10. The method of claim 3 wherein the compound is applied several times a day.

11. The method of claim 1 wherein the compound is applied with gauze bandages soaked in the compound.

12. The method of claim 3 wherein the compound is applied with gauze bandages soaked in the compound.

13. The method of claim 1 wherein the compound is applied orally and swished and expectorated or swallowed.

14. The method of claim 3 wherein the compound is applied orally and swished and expectorated or swallowed.

15. The method of claim 3 wherein $R_1$ is an amino acid.

16. The method of claim 4 wherein $R_1$ is an amino acid.

17. The method of claim 15 wherein the amino acid is selected from the group consisting of lysine and arginine.

18. The method of claim 16 wherein the amino acid is selected from the group consisting of lysine and arginine.

19. The method according to claim 3 wherein $R_1$ is an amine-containing antibiotic.

20. The method according to claim 4 wherein $R_1$ is an amine-containing antibiotic.

21. The method according to claim 19 wherein the antibiotic is selected from the group consisting of erythromycin, propionylerythromycin, neomycin, gentomycin, tobramycin, and mechlocycline.

22. The method according to claim 19 wherein the antibiotic is selected from the group consisting of erythromycin, propionylerythromycin, neomycin, gentomycin, tobramycin, and mechlocycline.

23. The method according to claim 1 wherein N-acetylcysteine is administered as the sodium salt.

24. The method according to claim 2 wherein N-acetylcysteine is administered as the sodium salt.

25. The method of claim 1 wherein the disease is pemphigus.

26. The method of claim 1 wherein the disease is bullous pemphigoid.

27. The method of claim 1 wherein the disease is cicatricial pemphigoid.

28. The method of claim 1 wherein the disease is lichen planus.

29. The method of claim 1 wherein the disease is canker sores (aphthons ulcers).

30. The method of claim 2 wherein the disease is pemphigus.

31. The method of claim 2 wherein the disease is bullous pemphigoid.

32. The method of claim 2 wherein the disease is cicatricial pemphigoid.

33. The method of claim 2 wherein the disease is lichen planus.

34. The method of claim 2 wherein the disease is canker sores (aphthons ulcers).

35. The method of claim 3 wherein the disease is pemphigus.

36. The method of claim 3 wherein the disease is bullous pemphigoid.

37. The method of claim 3 wherein the disease is cicatricial pemphigoid.

38. The method of claim 3 wherein the disease is lichen planus.

39. The method of claim 3 wherein the disease is canker sores (aphthons ulcers).

40. The method of claim 4 wherein the disease is pemphigus.

41. The method of claim 4 wherein the disease is bullous pemphigoid.

42. The method of claim 4 wherein the disease is cicatricial pemphigoid.

43. The method of claim 4 wherein the disease is lichen planus.

44. The method of claim 4 wherein the disease is canker sores (aphthons ulcers).

45. The method of claim 3 or 4 wherein $R^2$ is selected from the group consisting of the residue of lauric, oleic, caproic, linoleic, linolenic, caprylic, capric, perlargonic, neononanoic, neodecanoic, palmitelaidoic, myristic, palmitic, stearic, arachidic, behenic, lignoceric, heptanoic, nonanoic, undecanoic, tridecanoic, pentadecanoic, heptadecanoic, nonadecanoic, heneicosanoic, tricosanoic, arachidonic, docosahexanoic, elaidic, erucic, nervonic, palmitoleic or petriselinic acid.

46. The method of claim 3 or 4 wherein $R^2$ is selected from the group consisting of the residue of cromolyn, nedocrimil, or other mast cell stabilizers, azelaic acid, or methotrexate.

47. The method of claim 3, wherein said alkyloxyalkyl is methoxymethyl and said aryloxyalkyl is phenoxymethyl.

48. The method of claim 4, wherein said alkyloxyalkyl is methoxymethyl and said aryloxyalkyl is phenoxymethyl.

* * * * *